United States Patent [19]

Agee et al.

[11] Patent Number: 4,922,896

[45] Date of Patent: May 8, 1990

[54] COLLES' FRACTURE SPLINT

[75] Inventors: John M. Agee, 77 Scripps Dr., Suite 101, Sacramento, Calif. 95825; Francis C. King, Sacramento, Calif.

[73] Assignee: John M. Agee, Sacramento, Calif.

[21] Appl. No.: 347,990

[22] Filed: May 5, 1989

[51] Int. Cl.⁵ ............................................. A61F 5/04
[52] U.S. Cl. ....................................... 606/55; 606/57
[58] Field of Search ....... 128/92 VK, 92 VD, 92 ZZ, 128/92 V, 84 B, 84 C, 69, 92 R

[56] References Cited

U.S. PATENT DOCUMENTS

| | | | |
|---|---|---|---|
| 2,333,033 | 10/1943 | Mraz | 128/92 ZZ |
| 4,349,017 | 9/1982 | Sayegh | 128/92 A |
| 4,611,586 | 9/1986 | Agee et al. | 128/92 VD |

Primary Examiner—Robert A. Hafer
Assistant Examiner—Charles H. Sam
Attorney, Agent, or Firm—Dean P. Edmundson

[57] ABSTRACT

An improved splint is described for setting a Colles' fracture. The splint includes first, second and third elements connected together. A metacarpal bar is carried on the first element and is movable therealong. Two pins pass through the metacarpal bar and extend into a bone of a patient of one side of a bone fracture. The second element is pivotally mounted on one end of the first element for movement about an axis which forms an acute angle with respect to the longitudinal axis of the first element. The third element is pivotally mounted on the second element for movement about an axis which is perpendicular to the longitudinal axis of the second element. The third element includes transverse openings through which two pins extend which are inserted into the bone of a patient on the opposite side of the bone fracture. In one embodiment the metacarpal bar can be rotated about an axis parallel to the longitudinal axis of the first element.

15 Claims, 6 Drawing Sheets

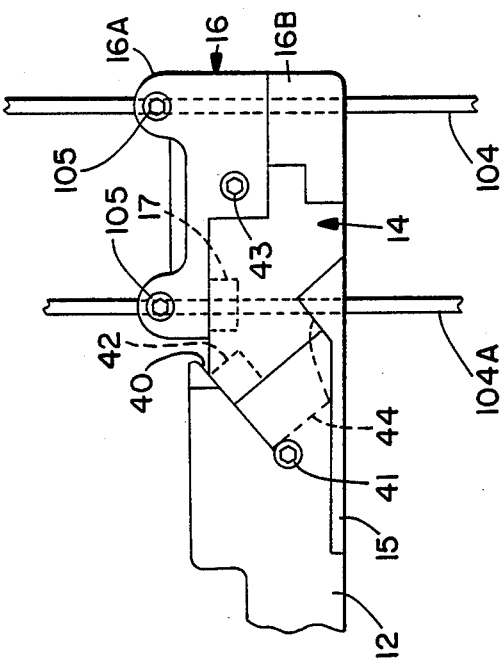
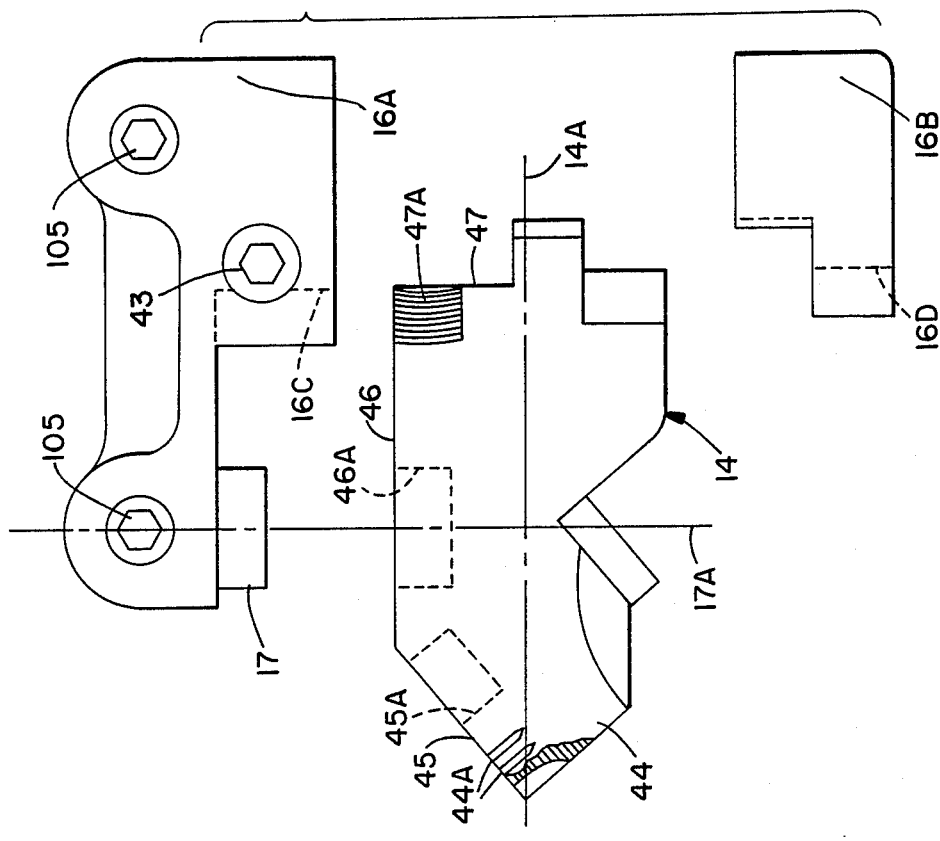

COLLES' FRACTURE SPLINT

FIELD OF THE INVENTION

This invention relates to mechanical splints for use in setting fractures of the human skeleton. More particularly, this invention relates to splints for use in setting fractures of the distal radius and/or wrist joint. Even more particularly, this invention relates to an improved articulated splint for use in setting Colles' fractures.

BACKGROUND OF THE INVENTION

Various devices have been previously used to set fractures of the distal radius in the forearm, but such devices have generally been unsatisfactory. External fixators (hereafter referred to as splints) which have been previously used have generally not been properly designed for selective and continuously adjustable degrees of distraction across the fracture site while allowing for independent adjustment for both appositional and rotational alignment of the same fracture so as to provide the capability of easily returning the distal and proximal fragments to their proper location and to hold them in such locations until the fracture has healed.

Another drawback associated with conventional splints used to treat a fracture is the fact that such splints are comprised of metallic parts, such as rods, screws and pinholding members which span the fracture site. Such metallic parts are opaque to x-rays and do not permit viewing of all aspects of a fracture site in x-ray photographs.

Another drawback with the use of conventional splints for treating a fracture is in the design deficiencies which prevent the selective displacement of the hand and thereby the wrist and distal fragment of the radius in a radial and ulnar direction while isolating this aspect of the fracture reduction from the other three aspects of the fracture reduction, namely, apposition in a dorsal-palmar direction, rotational alignment, and length or degree of distraction. Thus, with conventional splints, it is not possible to manipulate the fracture reduction in a radial and ulnar direction without losing the beneficial adjustments provided by the other three aspects of fracture reduction.

A further drawback associated with conventional splints is that they do not allow for selective extension and flexion of the wrist joint itself. Such extension and flexion can frequently facilitate fracture reduction and/or minimize the risks of extensor tendon "overpull" through wrist extension. Specifically, wrist extension relaxes the tension on the finger extensor tendons and thereby minimizes the risk of producing a stiff hand by allowing more flexion of the metacarpophalangeal joints of the fingers.

U.S. Pat. No. 4,548,199 describes two embodiments of a fracture splint, one of which provides distraction of the distal and proximal bone fragments relative to a fracture site and the other being designed to project an axis from its two major moveable parts that becomes coincident with the rotational axis about which most Colles' type fractures typically rotate. Both of these embodiments have metallic parts which render it difficult to provide x-ray photographs of the fracture site with the splint in place. Moreover, neither embodiment allows for selective adjustment of appositional alignment as appreciated from the anterior-posterior x-ray view, i.e., adjustments of the radioulnar alignment of the fracture. Further, neither embodiment allows for wrist flexion and extension.

U.S. Pat. No. 4,611,586, incorporated herein by reference, describes an improved splint especially for use in treating a Colles' type fracture. Such splint includes an elongated distal element having a traveling block which is movable along the length thereof. One or two distal pins can be carried by the block, the pins being insertable into the metacarpal of the index finger to secure skeletal fixation on the distal side of the fracture site.

A proximal element is pivotally mounted on the proximal end of the distal element and is provided with a pair of pin-receiving holes therethrough. Adjustment means between the distal and proximal elements effects pivotal movement of these two elements relative to each other. Such adjustment means is preferably in the form of a worm and worm gear configured to allow one of the pins to pass through the worm gear and to be inserted into the proximal fragment without interference with the worm gear itself. A worm and rack is preferably used to move the traveling block relative to the distal element.

The distal element of such splint can be made of rigid high strength plastic substantially transparent to x-rays. This permits viewing of the fracture site at all angles in an x-ray photograph, thereby improving the quality of assessment of alignment and enhancing the healing rate. The splint is constructed to allow the distal element of the splint to carry the hand, the wrist and the distal fragment of the fractured radius about an arc with respect to the proximal element of the splint when the proximal element is attached to the radius on the proximal side of the fracture site. The main biomechanical contribution of the splint is the way in which the splint biomechanically complements the pathomechanics of a Colles' type fracture by reducing the fracture displacement about the same axis through which the fragments are displaced at the time of the injury.

In another version of the traveling block on the distal element, the splint has the capability of permitting selective movement of the hand and thereby the wrist and distal fragment of the radius in a radial and ulnar direction by use of a simple adjustment device, such as a wing nut, which can be moved or rotated on the modified traveling block. Moreover, the modified traveling block is designed to allow for selective extension and flexion of the wrist while permitting distracting forces to restore proper length to the radius bone.

The splint also allows selective alignment of the fracture in one plane and/or about one axis of its evolution without substantially altering the alignment in another plane and/or axis. Further, the splint allows for radial and ulnar displacement of the hand on the forearm and thereby displaces the fracture in radial and ulnar directions in a manner which isolates that aspect of the fracture reduction from the other three aspects of fracture reduction.

Although the splint described in U.S. Pat. No. 4,611,586 represented an improvement over previous devices, it does not provide for as many degrees of movement of the hand and wrist as are often required in the setting of a Colles' fracture.

There has not heretofore been provided an external fixator or splint having the advantages exhibited by the splint of the present invention.

SUMMARY OF THE PRESENT INVENTION

In accordance with the present invention there is provided an improved fracture splint which is especially useful for setting a Colles' type fracture of the distal radius. The improved splint comprises, in one embodiment:

(a) an elongated first element having a free end and a mounting end;

(b) an elongated metacarpal bar carried by said first element and being adjustably movable along said first element; said metacarpal bar including transverse openings therethrough for receiving and securing first and second pins thereto; wherein said pins are adapted to be inserted into a bone of a patient on one side of a bone fracture;

(c) a second element pivotally mounted on said mounting end of said first element for movement about an axis which forms an acute angle relative to the longitudinal axis of said first element; the pivotal movement of said second element relative to said first element being the only degree of freedom of said second element relative to said first element;

(d) a third element pivotally mounted on said second element for movement about an axis which is perpendicular to the longitudinal axis of said second element; said third element including transverse openings extending therethrough;

(e) third and fourth pins adapted to be received and secured in said transverse openings in said third element; wherein said third and fourth pins are adapted to be inserted into the bone of a patient on the opposite side of said bone fracture;

wherein the pivotal movement of said third element relative to said second element is the only degree of freedom of said third element relative to said second elements; and wherein said second element is adapted to pivot about said third pin.

The improved splint of the invention has all of the advantages exhibited by the splint of U.S. Pat. No. 4,611,586 and exhibits further advantages. The improved splint allows for pivotal movement of the splint about an axis which is perpendicular to the longitudinal centerline of the splint. The metacarpal bar can also be moved toward or away from the longitudinal axis of the splint for fine tuning appositional alignment of the hand in the radialulnar direction.

The distal portion of the splint can be formed of plastic which is transparent to x-rays, yet the splint has high strength so that x-ray photographs of the fracture site can be made with the splint in place and without affecting adjustments of the splint.

The metacarpal bar can also be pivoted at one of its ends in a manner such that wrist extension or flexion can be adjusted. The axis of the extension-flexion adjustment extends to the center of the wrist joint.

Another advantage of the splint of this invention is that the metacarpal bar can be pivoted or rotated about a longitudinal axis. This can be a very important advantage when the distal pins are not in a plane which is parallel to the plane in which the proximal pins are located.

Other advantages of the improved fracture splint of the invention will become apparent from the following detailed description and the appended drawings.

BRIEF DESCRIPTION OF THE DRAWINGS

The invention is described in more detail hereinafter with reference to the accompanying drawings, wherein like reference characters refer to the same parts throughout the several views and in which:

FIG. 5 is a top, exploded view illustrating the second and third elements of the fracture splint of the invention;

FIG. 5A is a side elevational view of a worm useful in the splint of the invention;

FIG. 6 is a top view of the proximal end of the fracture splint of the invention;

DETAILED DESCRIPTION OF THE INVENTION

Figure 1:
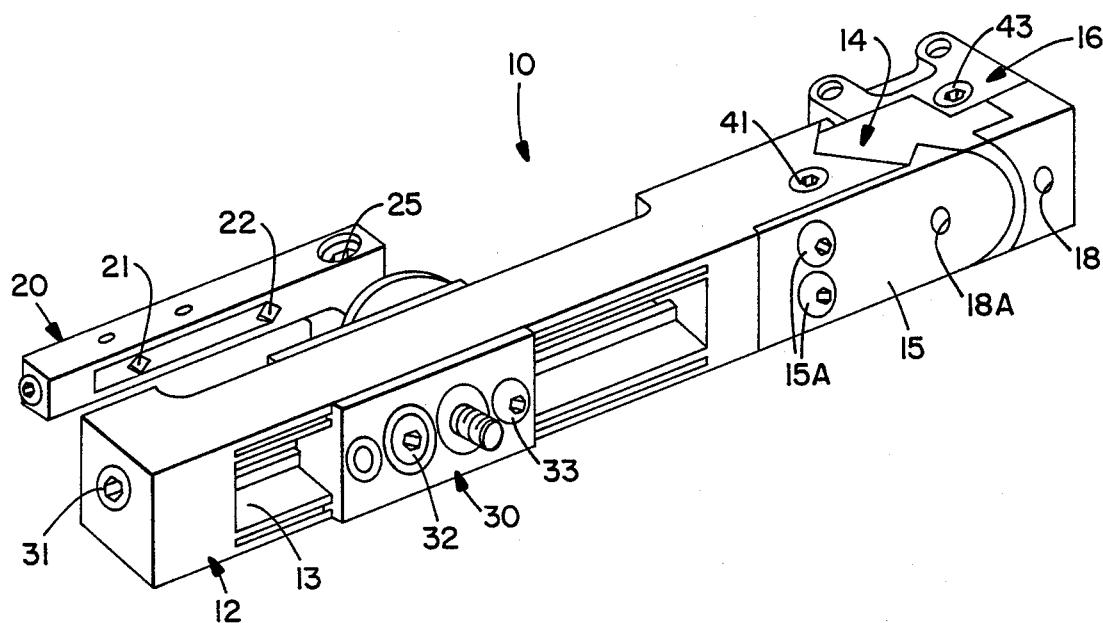
FIG. 1 is a perspective view of one embodiment of the improved fracture splint of the invention.

The improved fracture splint or external fixator 10 of the invention is illustrated in the accompanying drawings. The splint includes an elongated support or distal element 12 which is longitudinally straight and preferably is an integral element composed of rigid plastic or other suitable x-ray transparent structurally strong material. This element can be molded or machined and must have sufficient strength to withstand the bending movements placed on it by the various muscles which cross and thereby deform the fracture site.

Element 12 is shown generally as having a rectangular cross-section. Preferably it includes an elongated longitudinal slot 13, as illustrated in the drawings.

The proximal end of element 12 is attached to a second element 14 which is in turn pivotally attached to third element 16. An elongated metacarpal bar 20 is attached or connected to moving means 30 which is carried in the slot 13 of element 12.

Figure 2:
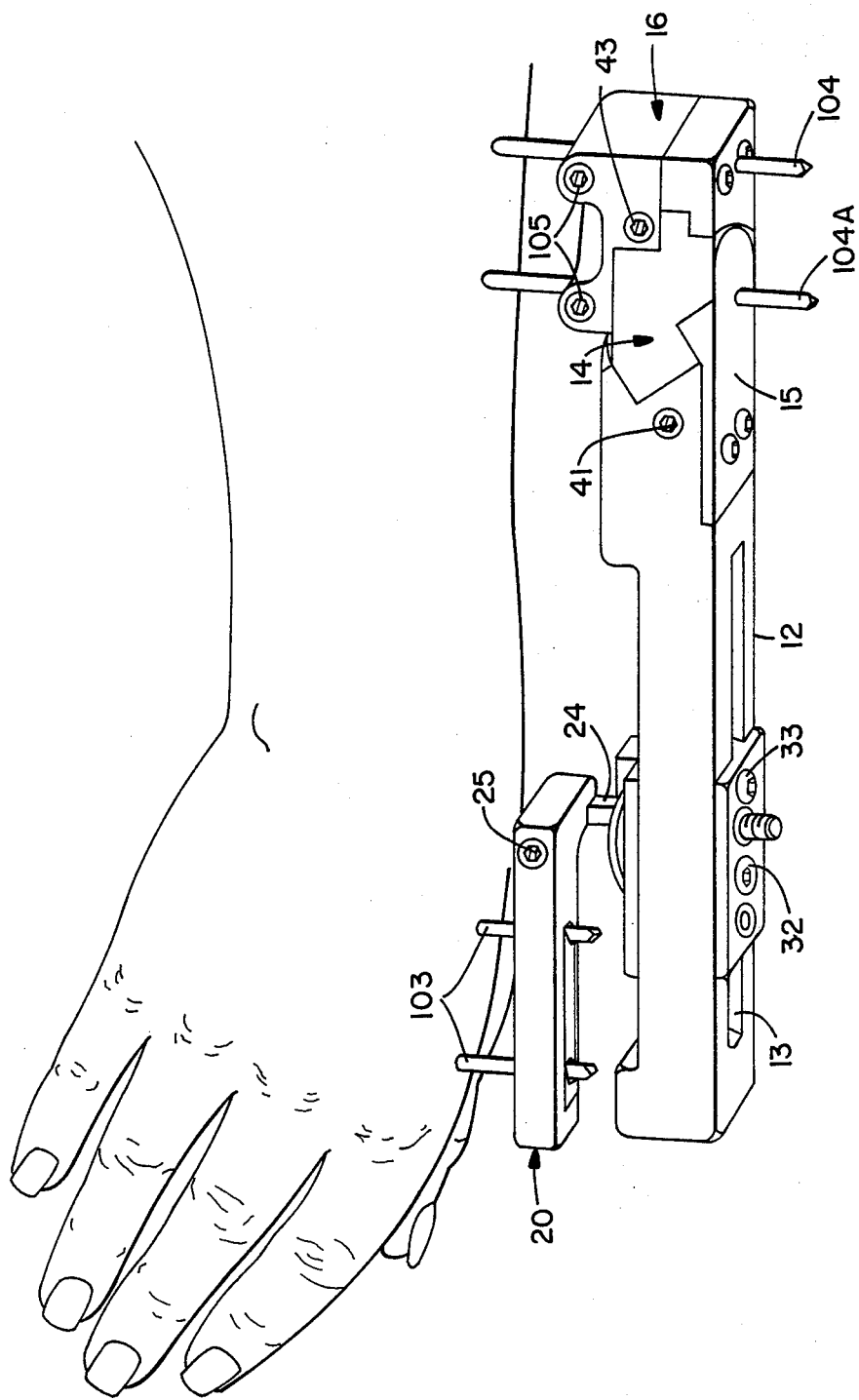
FIG. 2 is a perspective view of the improved fracture splint of the invention secured in an operative position on the radial aspect of the patient's; forearm.
Figure 4:
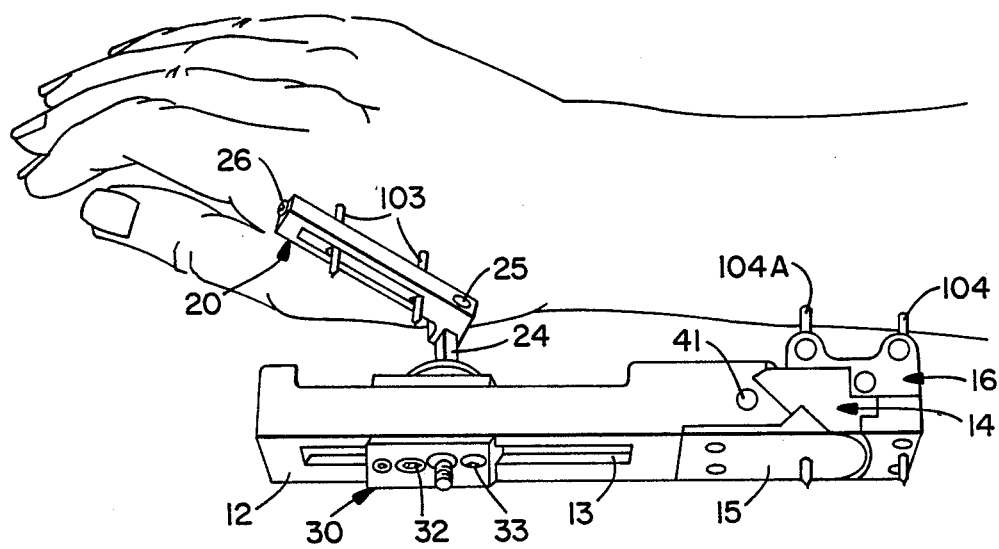
FIG. 4 is a perspective view of the improved splint secured on a patient's forearm and illustrating pivoting of the metacarpal bar at its mounting end to provide adjustment for wrist extension or flexion.

The metacarpal bar is spaced from and generally parallel to the first element 12, as illustrated. Two openings or apertures 21 and 22 extend transversely through the metacarpal bar 20 for receiving and securing two distal pins therein. The pins are shown in FIGS. 2 and 4, for example, and are adapted to be inserted into the index metacarpal on one side of the fracture site.

Figure 1A:
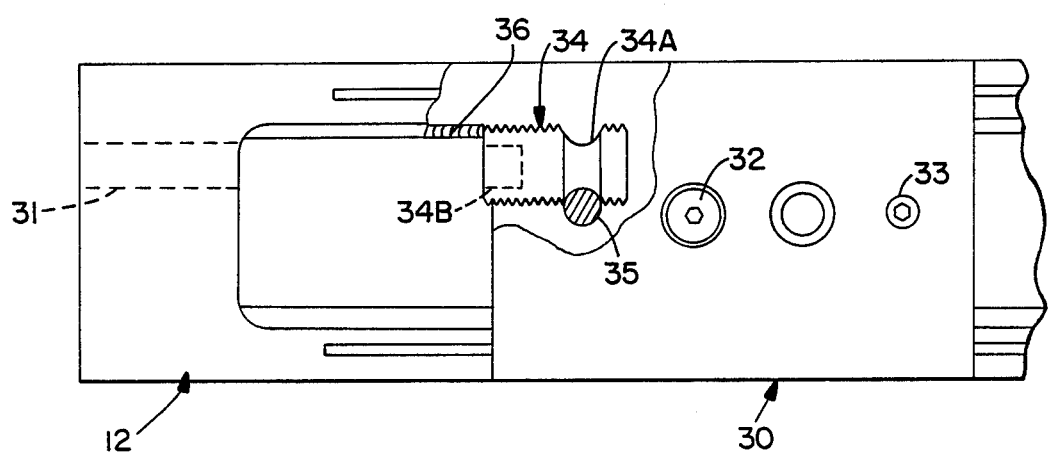
FIG. 1A is a side elevational, partially cut-away, view illustrating means for moving the movable block along the first element of the splint of FIG. 1.

The moving means or trolley 30 is adapted to be moved longitudinally along the slot 13 in element 12. An Allen screwdriver is inserted into the head 34B of a socket on screw 34 accessible through an opening 31 at the distal end of element 12. An appropriate gear means operatively connected between moving means 30 and the socket causes the moving means to move longitudinally along the slot in element 12 in response to rotation of the socket. When the socket is rotated in a clockwise manner the moving means is moved toward the proximal end of element 12 (i.e., toward the fracture site). Rotation in the opposite direction causes the moving means to move toward the distal end of element 12. FIG. 1A illustrates one manner in which the movement of trolley 30 is controlled. Socket or screw 34 is carried by trolley 30. An Allen wrench can be inserted through opening 31 in element 12 in order to be slidably received in the recess in head portion 34B of screw 34. Spaced teeth members or threads 36 along element 12 are engaged by the threads of screw 34. Screw 34 includes a groove or notch 34A which extends completely around screw 34. Bolt or screw 35, which is also carried by trolley 30, extends transversely through trolley 30 and is positioned such that it extends through groove 34A to one side of screw 34, as illustrated. This arrangement enables screw 34 to be rotated, as desired, to cause trolley 30 to be moved along element 12. Bolt or screw 35 does not interfere with the rotation of screw 34 but it does maintain the longitudinal position of screw 34 relative to trolley 30.

One end of the metacarpal bar 20 is mounted on a square or rectangular shaft 24 (shown in FIGS. 2 and 4) which extends outwardly from moving means or trolley 30. Set screw 25 may be tightened to secure the metacarpal bar to shaft 24 at a desired position.

Moving means 30 also includes appropriate gear means to enable movement of shaft 24 relative to means 30 to be fine tuned. By rotating socket 32 with an appropriate wrench, the shaft 24 (and hence metacarpal bar 20) may be caused to move laterally away from or closer to element 12 while maintaining the metacarpal bar 20 parallel to element 12. For example, if the distal fragment of the bone is displaced radially with respect to the proximal fragment, then the shaft 24 and metacarpal bar must be moved slightly farther away from element 12. Conversely, if the distal fragment of the bone is displaced in an ulnar direction, the shaft 24 and metacarpal bar 20 must be moved slightly closer to element 12.

Moving means or trolley 30 is preferably also made of x-ray transparent plastic. It may include a worm gear which is engaged by an elongated worm connected to a socket. Alternatively, both the trolley and the element 12 include threaded portions, e.g., a portion of the edge of the slot 13 may include threads which are engaged by a worm or screw supported by trolley 30. Upon rotation of the worm (or screw), the trolley 30 is caused to move longitudinally within slot 13.

The proximal end of element 12 includes an inclined face 40 from which a cylindrical mounting member or shank 42 projects. This is illustrated in FIG. 6. The mounting member 42 partially extends into a crescent-shaped or cylindrical recess formed by a concave inner face at the end of element 12, the axis of the concavity being coincident with the axis of mounting member 42.

Element 14 includes a convex or cylindrical end face 44 which is adapted to be complementally received within the concave recess at the end of element 12. This is illustrated in FIGS. 5 and 6. Element 14 includes a bore or recess 45A extending into an inclined face 45 thereof and the bore is adapted to rotatably receive mounting member 42, whereby element 14 can rotate about mounting member 42 relative to element 12. Plate 15 at the proximal end of element 12 assists retaining element 12 onto element 14. Screws 15A secure plate 15 in place.

Face 44 includes teeth 44A therealong. A worm 41 extends vertically through element 12 and engages teeth 44A. By rotation of worm 41 the element 12 is caused to pivot about the longitudinal axis of mounting member or shank 42. Such movement of element 12 is analogous to movement of element 12 along the surface of a cone.

Element 14 is pivotably connected to element 16. Face 46 of element 14 includes a recess 46A for receiving cylindrical shank 17 of element 16.

Face 47 of element 14 is convex and includes teeth 47A. Portion 16A of element 16 includes a concave recessed area 16C for receiving the convex face 47 of element 14. Portion 16B of element 16 also includes a recessed area 16D for receiving a portion of the convex face 47 of element, 14, as illustrated in FIG. 5.

Worm 43 extends vertically through element 16 and engages the teeth 47A of element 14. By rotating worm 43 (also illustrated in elevation in FIG. 5A), the element 14 is caused to pivot about shank 17. The central axis 17A of shank 17 is perpendicular to the longitudinal centerline of element 14, and the element 14 (and element 12) are caused to pivot about such axis which is perpendicular to the longitudinal axis 14A of element 14. Ideally, the longitudinal axis of the element 16 is parallel to the longitudinal axis of the radius (i.e., the bone to which pins 104 are secured in the arm of the patient).

Proximal pin 104 is adapted to extend through a transverse opening or aperture 18 through element 16, as illustrated. Proximal pin 104A is adapted to extend through a transverse opening or aperture 18A which extends through plate 15, element 14, and element 16. Pins 104A and 104 may be secured in place by means of set screws 105.

FIG. 4 illustrates another feature of the splint 10 of the invention. By rotation of screw 33, shaft 24 is unlocked so that it can be rotated in either a clockwise or counterclockwise direction, as desired. This causes the metacarpal bar to tilt upwardly or downwardly, as desired. In FIG. 4 the metacarpal bar 20 is shown tilted upwardly. This type of adjustment is for obtaining the desired position of wrist flexion or extension. The axis of the flexion-extension adjustment extends to the center of the wrist joint. After the metacarpal bar has been moved to its desired position, screw 33 may be tightened so as to lock shaft 24 against any further rotation.

Figure 7:
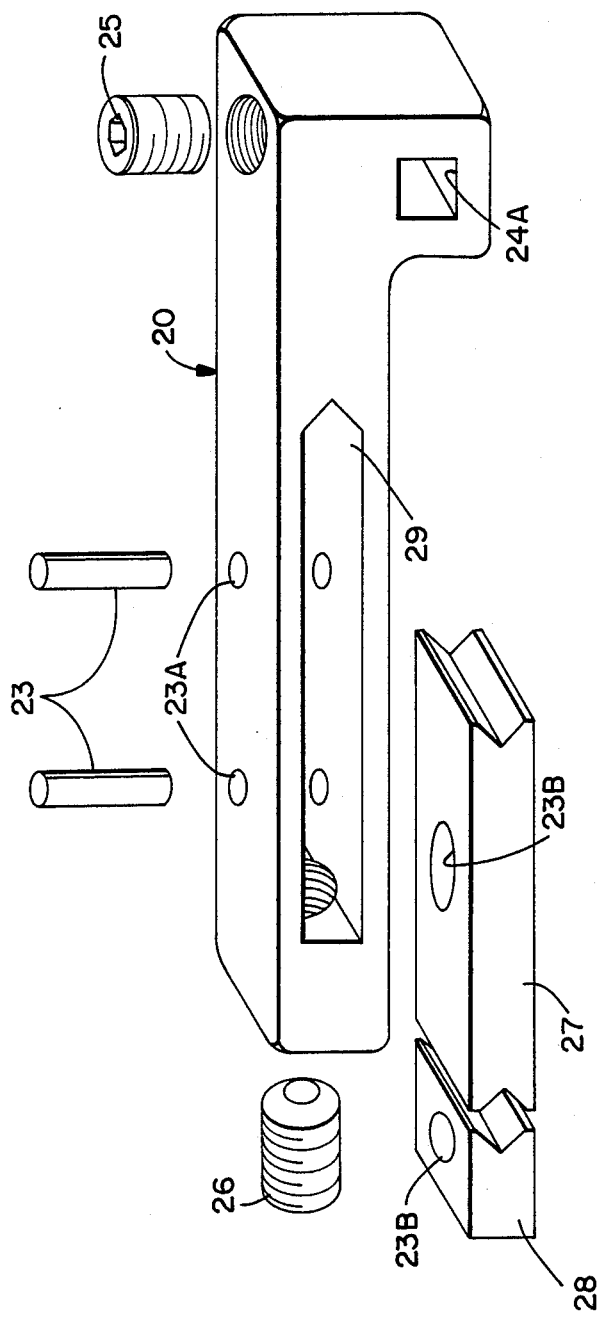
FIG. 7 is an exploded view illustrating one embodiment of metacarpal bar which is useful in this invention.

FIG. 7 illustrates one embodiment of metacarpal bar 20 of the invention. One end of the bar includes a transverse opening 24A (preferably having square cross-section or other suitable rotationally lockable geometry) for receiving shaft 24. Set screw 25 is for securing the bar 20 to shaft 24.

Bar 20 also includes a longitudinal opening 29 or slot in which spacers 27 and 28 may be received. Both ends of spacer 27 are chamfered, one end of spacer 28 is chamfered, and one end of slot 29 is chamfered. When the spacers are inserted into slot 29, as illustrated in FIG. 1, they define openings 21 and 22 for receiving distal pins 103 (as illustrated in FIGS. 2 and 4). Set screw 26 in the outer end of bar 20 is adapted to urge spacers 27 and 28 toward each other and towards the opposite end of slot 29. This causes both of the distal pins 103 to be securely clamped in the metacarpal bar. Retention pins 23 extend through registering apertures 23A and 23B in bar 20 and spacers 27 and 28 so as to retain the spacers in place.

Figure 8:
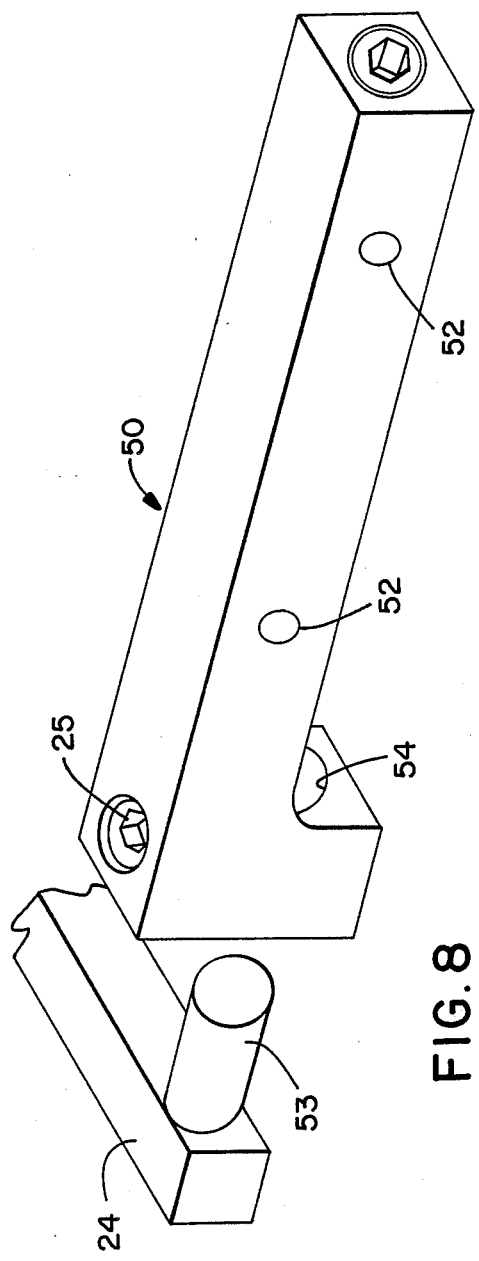
FIG. 8 is an exploded view illustrating another embodiment of metacarpal bar of this invention.

FIG. 8 illustrates another embodiment of metacarpal bar 50 which is useful in the invention. In this embodiment the mounting end of the metacarpal bar includes a circular opening or recess 54 which is adapted to slidably engage cylindrical shaft or stud 53 carried on shaft 24. This mounting arrangement enables the metacarpal bar 50 to be pivoted relative to stud 53 (i.e., bar 50 can be pivoted about an axis which is parallel to its longitudinal axis). Set screw 25 is used to lock the metacarpal bar 50 in any desired rotational position.

Apertures 52 extend transversely through bar 50 for receiving distal pins 103 therein. When the distal pins are not located in a plane parallel to pins 104 (i.e., when pins 103 are tilted upwardly or downwardly relative to pins 104) it is very desirable to be able to rotate the metacarpal bar 50 to enable the pins 103 to be received in apertures 52.

Figure 9A:
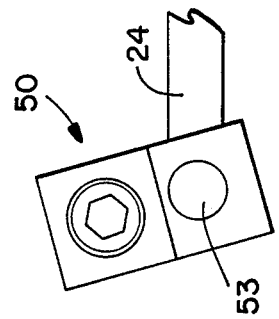
FIGS. 9A, B and C are end views of the metacarpal bar of FIG. 8 showing the manner in which the bar may be pivoted about an axis parallel to the longitudinal axis of the bar.
Figure 9B:
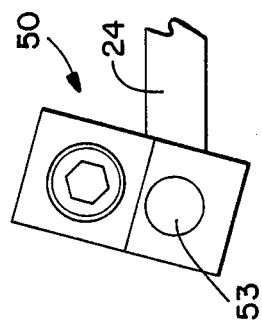
Figure 9C:
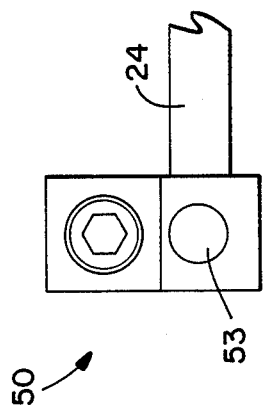

FIGS. 9A B and C are end views of bar 50 mounted on shank or stud 53 and illustrate the ability of the metacarpal bar to be rotated relative to shank or stud 53.

The angular adjustment between support element 12 and element 14 is achieved by rotation of worm 41. This causes element 12 to rotate relative to element 14 and thereby allows the distal portion of the splint to carry the hand, the wrist and the distal fragment of the radius about an arc with respect to the proximal fragment of the radius and its attached portion of the splint.

As explained above, the metacarpal bar may also be separately adjust to selectively move the hand (and thereby the wrist and distal fragment) in either a radial or ulnar direction, as desired.

The proximal pins 104 and 104A are inserted into the bar portion of the radius which is exposed by retracting the brachioradialis (BR) volarly and then by retracting the abductor pollicis longus (APL) and extensor pollicis brevis (EPB) dorsally, thereby exposing the radial shaft at and just distal to the pronator teres (PT). Insertion of pins 103, 104, and 104A is explained and illustrated in our prior U.S. Pat. No. 4,611,586, incorporated herein by reference.

Once the splint 10 is mounted on the distal and proximal pins, the various set screws are tightened to secure the pins to the splint. After the placement of the splint on the pins, the first step is usually to distract the fracture splint such that the overall length between the two sets of pins is increased, restoring appropriate length to the fractured radius by transmitting traction forces to the proximal and distal fragments. This is accomplished by moving the block 30 axially with respect to the distal portion or support element 12 and away from the proximal pins 104. After distraction, the length of the radius is restored. It is important that the radius not be overly distracted. Thus, there should be no gap between the distal fragment and the proximal fragment of the radius.

Figure 3:
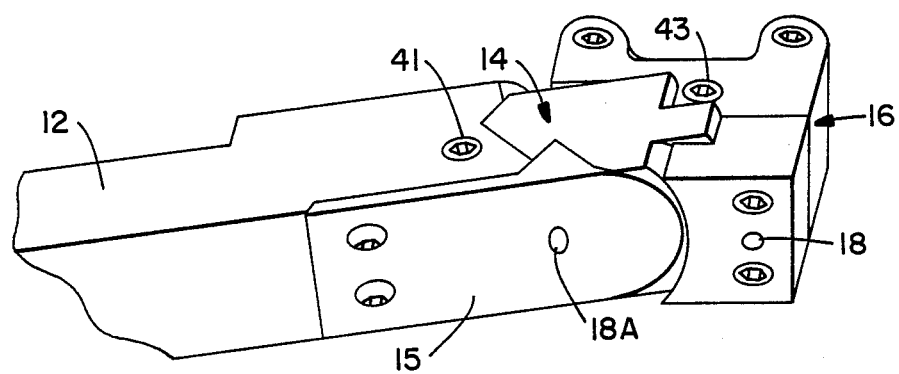
FIG. 3 is a perspective view of the proximal end of the improved splint of the invention

The pivotal adjustment of element 14 relative to element 16 is illustrated in FIG. 3. By rotating worm 43 the element 14 is caused to pivot about shank 17 which is perpendicular to the longitudinal centerline of element 14. This is a very desirable type of permissible adjustment for properly aligning the distal fragment with the proximal fragment of the radius.

By achieving the proper alignment of the distal fragment of the radius with respect to the forearm and proximal fragment of the radius, proper healing can be obtained in a manner in which complications are avoided.

Other variants are possible without departing from the scope of this invention.

What is claimed is:

1. A fracture splint comprising:
   (a) an elongated first element having a free end and a mounting end;
   (b) an elongated metacarpal bar carried by said first element and being adjustably movable along said first element; said metacarpal bar including transverse openings therethrough for receiving and securing first and second pins thereto; wherein said pins are adapted to be inserted into a bone of a patient on one side of a bone fracture;
   (c) a second element pivotally mounted on said mounting end of said first element for movement about an axis which forms an acute angle relative to the longitudinal axis of said first element; the pivotal movement of said second element relative to said first element being the only degree of freedom of said second element relative to said first element;
   (d) a third element pivotally mounted on said second element for movement about an axis which is perpendicular to the longitudinal axis of said second element; said third element including transverse openings extending therethrough;
   (e) third and fourth pins adapted to be received and secured in said transverse openings in said third element; wherein said third and fourth pins are adapted to be inserted into the bone of a patient on the opposite side of said bone fracture;
wherein the pivotal movement of said third element relative to said second element is the only degree of freedom of said third element relative to said second element; and wherein said second element is adapted to pivot about said third pin.

2. A fracture splint in accordance with claim 1, further comprising moving means on said first element for moving said metacarpal bar along said first element; wherein said moving means comprises meshing threaded portions on said moving means and said first element; wherein said moving means is adapted to selectively move said metacarpal bar along the length of said first element.

3. A fracture splint in accordance with claim 2, wherein said first element includes a longitudinally extending slot, and wherein said moving means is mounted in said slot.

4. A fracture splint in accordance with claim 1, further comprising first gear means coupled to said first element and second element for pivoting said second element relative to said first element.

5. A fracture splint in accordance with claim 4, wherein said gear means comprises a worm and a worm gear which mesh with each other.

6. A fracture splint in accordance with claim 2, wherein said metacarpal bar includes a free end and a mounting end; wherein said metacarpal bar is parallel to the longitudinal axis of said first element; wherein said mounting end of said metacarpal bar is connected to said moving means by a shaft which is perpendicular to said first element.

7. A fracture splint in accordance with claim 6, wherein said metacarpal bar is adapted to be rotated about said shaft.

8. A fracture splint in accordance with claim 7, wherein said shaft includes a stud member perpendicular thereto; and wherein the longitudinal axis of said metacarpal bar is parallel to the longitudinal axis of said stud member.

9. A fracture splint comprising:
(a) an elongated first element having a free end and a mounting end;
(b) an elongated metacarpal bar carried by said first element and being adjustably movable along said first element; said metacarpal bar including transverse openings therethrough for receiving and securing first and second pins thereto; wherein said pins are adapted to be inserted into a bone of a patient on one side of a bone fracture; wherein said metacarpal bar is further adapted to be moved toward and away from said first element;
(c) a second element pivotally mounted on said mounting end of said first element for movement about an axis which forms an acute angle relative to the longitudinal axis of said first element; the pivotal movement of said second element relative to said first element being the only degree of freedom of said second element relative to said first element;
(d) a third element pivotally mounted on said second element for movement about an axis which is perpendicular to the longitudinal axis of said second element; said third element including transverse openings extending therethrough;
(e) third and fourth pins adapted to be received and secured in said transverse openings in said third element; wherein said third and fourth pins are adapted to be inserted into the bone of a patient on the opposite side of said bone fracture;
wherein the pivotal movement of said third element relative to said second element is the only degree of freedom of said third element relative to said second element; and wherein said second element is adapted to pivot about said third pin.

10. A fracture splint in accordance with claim 9, further comprising moving means on said first element for moving said metacarpal bar along said first element; wherein said moving means comprises meshing threaded portions on said moving means and said first element; wherein said moving means is adapted to selectively move said metacarpal bar along the length of said first element.

11. A fracture splint in accordance with claim 10, wherein said first element includes a longitudinally extending slot, and wherein said moving means is mounted in said slot.

12. A fracture splint in accordance with claim 9, further comprising first gear means coupled to said first element and second element for pivoting said second element relative to said first element; wherein said gear means comprises a worm and a worm gear which mesh with each other.

13. A fracture splint in accordance with claim 10, wherein said metacarpal bar includes a free end and a mounting end; wherein said metacarpal bar is parallel to the longitudinal axis of said first element; wherein said mounting end of said metacarpal bar is connected to said moving means by a shaft which is perpendicular to said first element.

14. A fracture splint in accordance with claim 13, wherein said metacarpal bar is adapted to be rotated about said shaft.

15. A fracture splint in accordance with claim 14, wherein said shaft includes a stud member perpendicular thereto; and wherein the longitudinal axis of said metacarpal bar is parallel to the longitudinal axis of said stud member.

* * * * *